(12) United States Patent
Kemppainen et al.

(10) Patent No.: US 8,838,224 B2
(45) Date of Patent: Sep. 16, 2014

(54) METHOD, APPARATUS AND COMPUTER PROGRAM PRODUCT FOR PREDICTING VENTRICULAR TACHYARRHYTHMIAS

(75) Inventors: Reko Kemppainen, Lappeenranta (FI); Mikko Kaski, Espoo (FI)

(73) Assignee: General Electric Company, Schenectady, NY (US)

( * ) Notice: Subject to any disclaimer, the term of this patent is extended or adjusted under 35 U.S.C. 154(b) by 8 days.

(21) Appl. No.: 13/435,087

(22) Filed: Mar. 30, 2012

(65) Prior Publication Data

US 2013/0261479 A1  Oct. 3, 2013

(51) Int. Cl.
*A61B 5/04* (2006.01)

(52) U.S. Cl.
USPC ............................................. 600/517

(58) Field of Classification Search
None
See application file for complete search history.

(56) References Cited

U.S. PATENT DOCUMENTS

| | | | |
|---|---|---|---|
| 6,308,094 B1 | 10/2001 | Shusterman et al. | |
| 7,225,013 B2 | 5/2007 | Geva et al. | |
| 7,330,750 B2 | 2/2008 | Erkkila et al. | |
| 7,336,995 B2 * | 2/2008 | Armoundas et al. | 607/9 |
| 7,471,982 B2 | 12/2008 | Thong | |
| 2009/0326595 A1 * | 12/2009 | Brockway et al. | 607/3 |

OTHER PUBLICATIONS

Shusterman et al., "Upsurge in T-Wave Alternans and Nonalternating Repolarization Instability Precedes Spontaneous Initiation of Ventricular Tachyarrhythmias in Humans", DOI: 10.1161, CIRCULATIONAHA.105.607895, Circulation published online Jun. 19, 2006.

* cited by examiner

*Primary Examiner* — Christopher D Koharski
*Assistant Examiner* — Elizabeth K So
(74) *Attorney, Agent, or Firm* — Andrus Intellectual Property Law, LLP

(57) ABSTRACT

A method, apparatus, and computer program product for predicting ventricular tachyarrhythmia (VTA) are disclosed. To provide a mechanism that allows prediction of VTA events efficiently within a few hours before the onset of the actual event, a set of repolarization parameters indicative of ventricular repolarization in a subject's heart is determined in successive time segments, thereby to obtain a time series of the set of repolarization parameters. Based on the time series, at least one change indication variable indicative of changes in the ventricular repolarization of the heart is produced and the risk of potential ventricular tachyarrhythmia is predicted based on the at least one change indication variable. (FIG. 1).

9 Claims, 4 Drawing Sheets

METHOD, APPARATUS AND COMPUTER PROGRAM PRODUCT FOR PREDICTING VENTRICULAR TACHYARRHYTHMIAS

BACKGROUND OF THE INVENTION

This disclosure relates generally to monitoring of electrocardiograms in patient monitors. More particularly, the present invention relates to prediction of ventricular tachyarrhythmias (VTAs) in patient monitors.

Patient monitors are electronic devices designed to display physiological information about a subject. Electrocardiogram (ECG), electroencephalogram (EEG), plethysmographic signals, and signals related to blood pressure, temperature, and respiration represent typical physiological information contained in full-size patient monitors. Patient monitors are typically also furnished with alarming functionality to alert the nursing staff when a vital sign or physiological parameter of a patient exceeds or drops below a preset limit. Alarms are normally both audible and visual effects aiming to alert the staff to a life-threatening condition or to another event considered vital. In most monitors, the alarm limits may be defined by the user, since the limits typically depend on patient etiology, age, gender, medication, and various other subjective factors. Each specific physiological parameter, such as heart rate or blood pressure, may also be assigned more than one alarm limit. Furthermore, there is a lot of data trended and available for caregivers to be reviewed in a patient monitor.

For recording an electrocardiogram, electrocardiographic leads are used at specified locations of the subject for recording ECG waveforms. In typical clinical practice, 12 leads are used to the record the ECG. However, the number of leads used may vary. Each lead records a waveform representing the electrical activity generated by the heart cardiac cycle by cycle and together the lead recordings provide spatial information about the heart's electrical activity.

A normal cardiac cycle includes contractions of the atrial muscles, which are activated by the autonomic sinoatrial node (SA node), also called the sinus node. An electrophysiologic (EP) signal generated by the SA node spreads in the right and left atrium leading to their contraction. The EP signal further reaches the atrioventricular node (AV node) situated between the atria and the ventricles. The AV node delays the EP signal, giving the atria time to contract completely before the ventricles are stimulated. After the delay in the AV node, the EP signal spreads to the ventricles via the fibers of the His-Purkinje system leading to the contraction of the ventricles. After the contraction, the atria are relaxed and filled by blood coming from venous return. The entire cardiac cycle is a combination of atrial and ventricular contractions, i.e. depolarizations, and relaxations, i.e. repolarizations.

Cardiovascular disease is currently the most common single cause of natural death in developed countries. Sudden cardiac death (SCD) is estimated to account for approximately 50 percent of these deaths. Ventricular tachyarrhythmias (VTAs) are thought to be the most common primary cause of SCD and also the most dangerous heart rhythm disturbances. Ventricular tachyarrhythmias refer to tachycardias, or fast heart rhythms, that originate from lower ventricles of the heart. Ventricular tachyarrhythmias include ventricular tachycardia (VT) and ventricular fibrillation (VF). Prolonged ventricular arrhythmias may lead to a completely pulseless state called asystole (ASY).

Mechanisms of ventricular tachyarrhythmias are known and rather well studied. The ultimate cause of a ventricular tachyarrhythmia is a critical alteration in the electrical properties of cardiac myocotes. Due to this, the electrical activation does not originate from the AV node and/or does not propagate in the ventricles in a normal way. Although the arrhythmogenic mechanisms are rather well known, the onset of ventricular tachyarrhythmia is not known. It may, however, be assumed that the mechanoelectric properties of the myocardium are altered prior to the onset. In recent years, various morphology related parameters and variability parameters, i.e. parameters related to the alterations and variability of heart beats, have been studied to find prognostic parameters for imminent ventricular tachyarrhythmia events. For example, multiple studies have been conducted to discover whether a spontaneous initiation of VTA and increased T wave alternans (TWA) have a causal relationship. These studies show, for example, increased TWA that peaks about 10 minutes before the onset of a VTA event. Despite the studies conducted, reliably precursors of VTAs have not been found, which is a manifestation of the complexity involved. In general, current research on precursors of VTAs is still in a rather disorganized and immature state that may be characterized by small sizes of databases that are not publicly available, by findings that are not independently reproduced, and by methods that are not clearly documented and standardized. Therefore, no technology exists at present for predictive VTA algorithms, but current patient monitors are able to detect VTA events only when they occur. This is a significant drawback since when a lethal arrhythmia occurs it may take up to several minutes before a rescue team is in position to start the resuscitation procedures. In this situation every second counts as damage to organs is most probably already occurring. It is estimated that the survival probability of a VTA patient decreases 7 to 10 percent with every minute of treatment delay.

Consequently, current patient monitor technology is not able to anticipate an imminent VTA event but can alert the nursing staff only when a VTA event is a reality. Reliable prediction of imminent VTA events would, however, greatly improve the survival chances of the patient, especially as efficient treatments, such as defibrillation, are commonly available.

BRIEF DESCRIPTION OF THE INVENTION

The above-mentioned drawback is addressed herein which will be comprehended from the following specification. In the disclosed method, parameters indicative of repolarization in a subject's heart are determined. Based on the parameter sets obtained in successive cardiac cycles, at least one variable indicative of changes in the repolarization is further determined. Typically, several variables indicative of both slow and fast changes in the repolarization may be determined, since a change may be very fast, occurring between adjacent beats, or very slow, taking up to hours to develop. The variable(s) is/are then employed to predict the risk of a potential ventricular tachyarrhythmia episode. In a further embodiment, one or more control parameters may be defined that indicate if a detected change in the repolarization is due to a benign change in patient's state, which explains the detected change in the repolarization and does not increase the risk of ventricular tachyarrhythmia.

In an embodiment, a method for predicting ventricular tachyarrhythmia comprises determining a set of repolarization parameters indicative of ventricular repolarization in a subject's heart, wherein the determining is performed in successive time segments, thereby to obtain a time series of the set of repolarization parameters. The method further includes producing, based on the time series, at least one change indication variable indicative of changes in the ventricular repolarization of the heart and predicting the risk of potential ventricular tachyarrhythmia based on the at least one change indication variable.

In another embodiment, an apparatus for predicting ventricular tachyarrhythmia comprises a first parameter unit adapted to determine a set of repolarization parameters indicative of ventricular repolarization in a subject's heart, wherein the first parameter unit is adapted to determine the repolarization parameters in successive time segments, thereby to obtain a time series of the set of repolarization parameters. The apparatus further includes a change indicator unit adapted to produce, based on the time series, at least one change indication variable indicative of changes in the ventricular repolarization of the heart and a risk evaluation unit adapted to predict risk of potential ventricular tachyarrhythmia based on the at least one change indication variable.

In a still further embodiment, a computer program product for predicting ventricular tachyarrhythmia comprises a first program product portion adapted to determine a set of repolarization parameters indicative of ventricular repolarization in a subject's heart, wherein the first program product portion is adapted to determine the repolarization parameters in successive time segments, thereby to obtain a time series of the set of repolarization parameters. The computer program product further comprises a second program product portion adapted to produce, based on the time series, at least one change indication variable indicative of changes in the ventricular repolarization of the heart and a third program product portion adapted to evaluate risk of potential ventricular tachyarrhythmia based on the at least one change indication variable.

Various other features, objects, and advantages of the invention will be made apparent to those skilled in the art from the following detailed description and accompanying drawings.

DETAILED DESCRIPTION OF THE INVENTION

Figure 1:
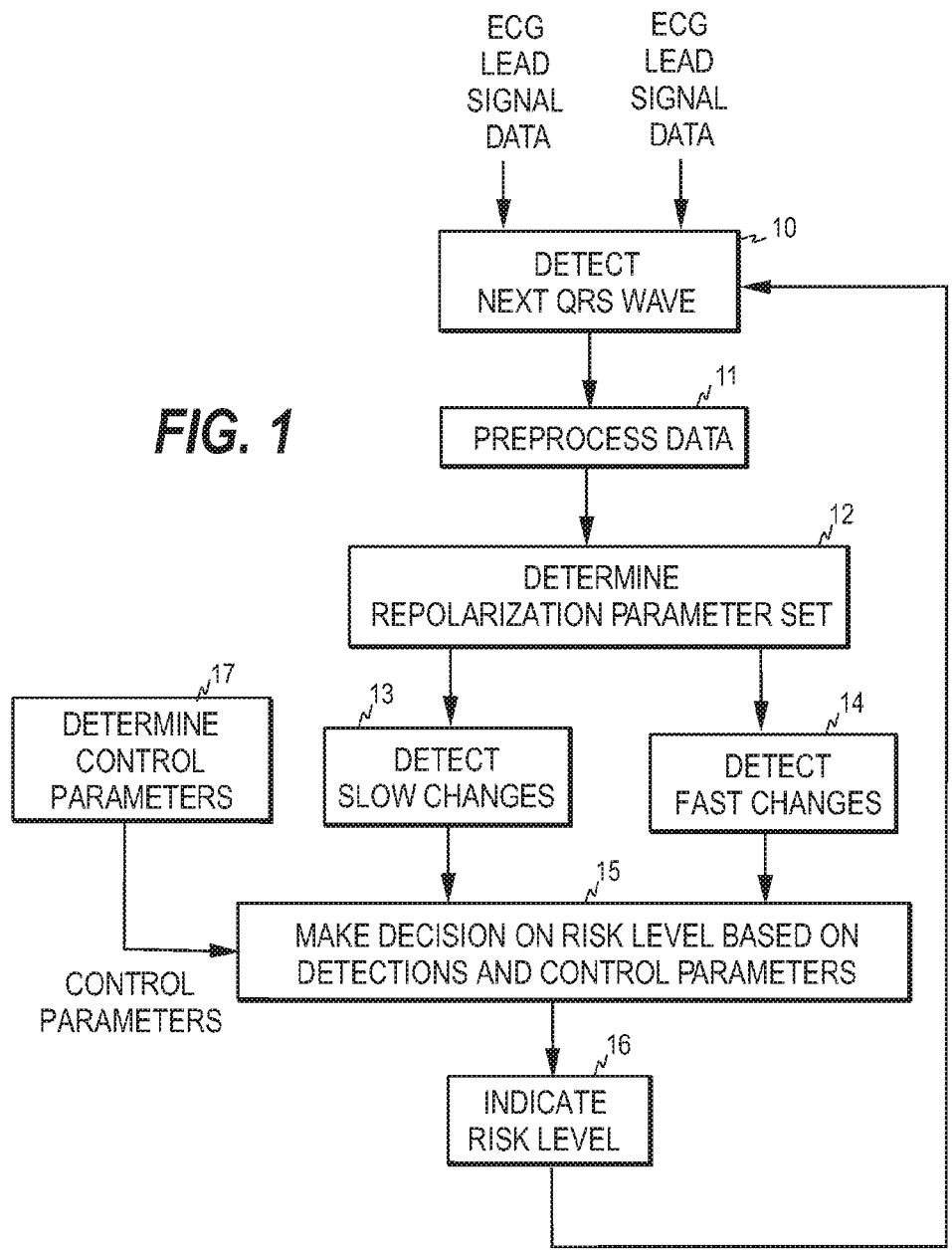
FIG. 1 illustrates one embodiment of the method for predicting an imminent ventricular tachyarrhythmia event.

FIG. 1 illustrates one embodiment of the method for predicting a ventricular tachyarrhythmia event. The steps shown in the figure correspond to one time segment, which typically corresponds to one cardiac cycle of the patient. In step 10, QRS complexes are detected from the multichannel ECG input data and the data is provided with annotations and fiducial points. Next, the signal data may be preprocessed in step 11. The preprocessing may include, for example, removal of high-frequency noise, baseline wander, and power line interference.

The actual predictive analysis of the signal data is initiated in step 12, in which a set of parameters is extracted from the data. There is consensus that repolarization changes and abnormalities play a major role in arrhythmia initiation and sustainability, and therefore the parameters determined in step 12 are indicative of ventricular repolarization of the heart and termed repolarization parameters in this context. The repolarization parameters may be divided into morphology parameters and variation parameters, depending on how they are measured from the signal. Morphology parameters describe morphology features within the repolarization phase, while variation parameters are indicative of variation occurring in the repolarization phase of the heart. Although the repolarization parameters may include any such quantities, five repolarization parameters may be employed in one embodiment of the method. These parameters are T wave amplitude, T wave asymmetry, T wave area, ST-level, and ST slope. The repolarization parameters are discussed in more detail below.

In the embodiment of FIG. 1, the repolarization parameters are supplied to parallel detection branches 13 and 14, in which repolarization changes are monitored and detected. In branch 13, slow changes are detected, while in branch 14 fast and more abrupt changes are detected. Furthermore, in this embodiment one or more control parameters are determined (step 17). A control parameter is a parameter that is employed to be able to discard changes the affect repolarization but are not related to real changes in the cardiac state or myocardial repolarization. Thus, the control parameter(s) generated make it possible to filter out false positive detections. The control parameter(s) may be determined separately or in connection with step 12 in which the repolarization parameters are determined.

The detection results from branches 13 and 14 and the control parameters are supplied to a decision-making step 15, in which the risk of occurrence of a VTA event is evaluated. In the embodiments discussed below, the evaluated risk may assume two values, high and low, depending on whether a ventricular tachyarrhythmia event is predicted or not. In the decision-making, the basic rule is that if a significant change is detected in either or both of the detection branches and the change(s) is/are not explained by any of the control parameters, a ventricular tachyarrhythmia event is predicted and an indication of increased risk of VTA is produced in step 16. Otherwise, a ventricular tachyarrhythmia event is not predicted and normal state is indicated in step 16.

Figure 2:
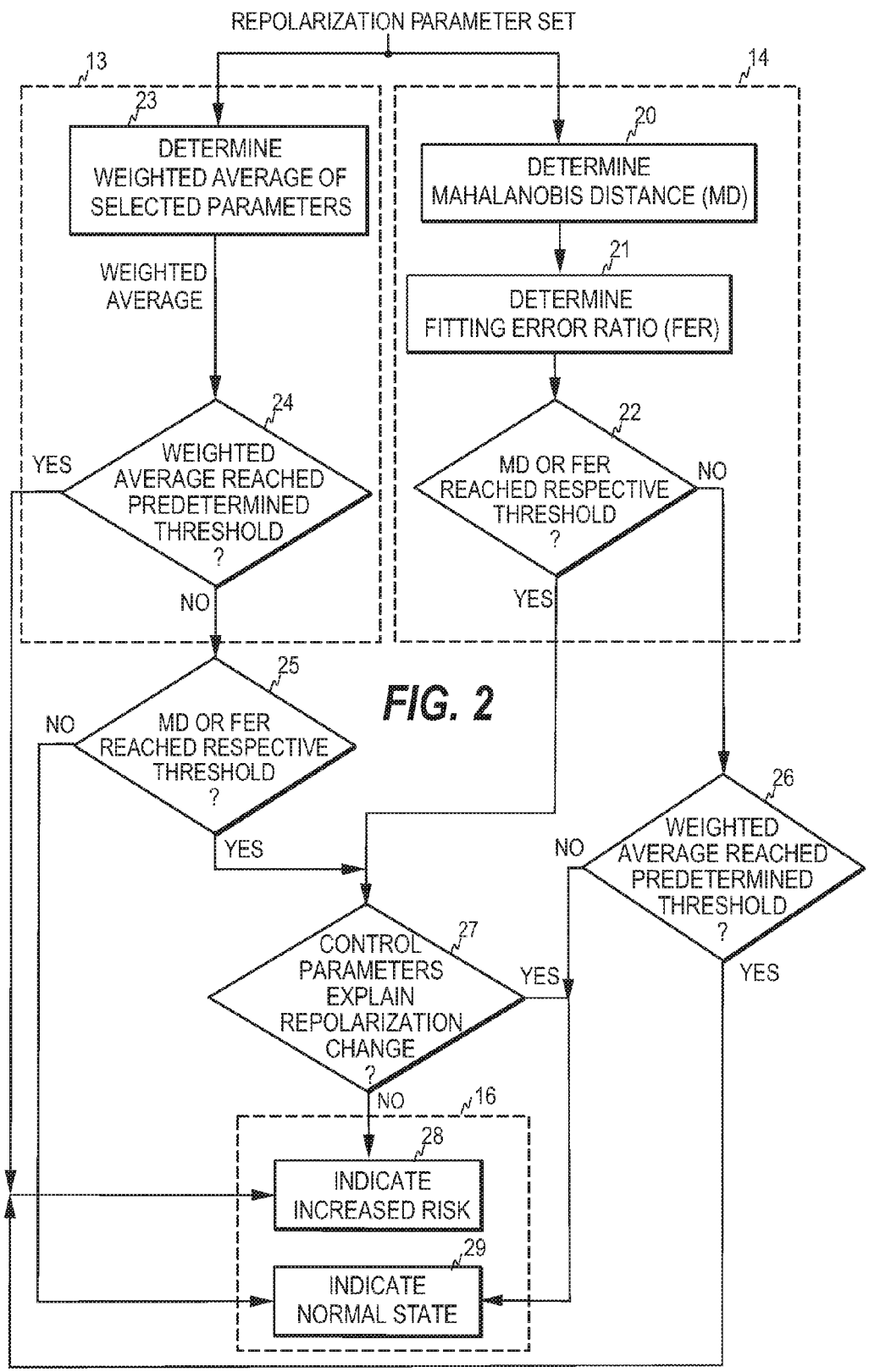
FIG. 2 illustrates an example of the change detection and decision-making processes carried out in the embodiment of FIG. 1.

FIG. 2 illustrates one embodiment of steps 13 to 16 of FIG. 1, i.e. the detection and decision-making processes. The repolarization parameters determined are supplied to both detection branches 13 and 14.

In branch 14, fast repolarization changes are detected by determining two change measures in two successive steps 20 and 21, respectively. In the first step 20, Mahalanobis distance (MD) between two successive repolarization parameter sets is determined, to obtain a measure of the magnitude of difference between the two sets. Unlike regular Euclidean norm, for example, Mahalanobis distance is scale invariant and takes into account the correlation between the parameters. The rationale for the utilization of Mahalanobis distance in the detection of a potentially life-threatening change in the state of the heart lies in the fact that the repolarization parameters correlate with heart rate and with each other. In this way, the Mahalanobis distance is insensitive to normal oscillation and changes predictable by earlier data, but larger distance is measured if the parameters do not "fit in the picture" of the covariance data involved. The Mahalanobis distance $d(x_i, x_{i-1})$ between adjacent parameter sets is defined by $d(x_i, x_{i-1}) = \sqrt{(x_i - x_{i-1})^T C^{-1} (x_i - x_{i-1})}$, where C is the covariance matrix.

Here, the parameters sets $x_i$ and $x_{i-1}$ are in vector form, in which the repolarization parameters form the components of the vector.

In the second step 21 of branch 14, a measure indicative of the change occurring in fitting error is determined. For this, the mutual dependency between a parameter and heart rate is estimated in order to be able to approximate the fitting error. The dependencies may be approximated for all or a subset of the repolarization parameters using, for example, first and second order polynomials that approximate the said dependency. However, any function or set of functions may be used to describe the dependency. The function(s)/polynomial(s) obtained for the parameters are termed a model in this context since they model the selected repolarization parameters as a function of heart rate.

A fitting error ratio (FER), i.e. a ratio of the fitting errors obtained for successive parameter sets, is used as the measure indicative of the change in the fitting error. The idea here is that as long as the model is able to predict the parameter values well enough, the ratio remains at a certain level. However, if there is a rapid and significant change in the repolarization, the prediction ability of the model drops, the fitting error increases, and the ratio changes significantly. To illustrate the determination of the fitting error and the change thereof mathematically, it is assumed again that vector x represents the repolarization parameter set. The corresponding heart rate or RR interval values may be stored in vector y. In order to calculate the fitting error ratio, a predefined number of segments may be used to fit the first and second order polynomial to the data. In general, the fitting may be carried out by solving the following overdetermined system for vector p: y=Ap, where p contains polynomial coefficients and A represents linear mapping between the coefficients and the measurements y. The LMSE (Linear Mean Square Estimate) for p may be calculated using the Moore-Penrose pseudoinverse: $\tilde{p}=A^+y$, where matrix $A^+$ is the Moore-Penrose pseudoinverse.

Next, the goodness of the fit is evaluated by calculating model-predicted values for the data used in fitting and for unseen future data $x_{fut}$. For fitted data $\tilde{y}=A\tilde{p}$ and for the future data $\tilde{y}_{fut}=A_{fut}\tilde{p}$. Finally, the fitting error is calculated as follows:

$$FER = \frac{\|y_{fut} - \tilde{y}_{fut}\|_2}{\|y - \tilde{y}\|_2},$$

where the double vertical line symbol with subscript 2 refers to Euclidian norm. Thus, FER represents the ratio of the goodness of a new prediction (numerator) to the goodness of a previous prediction (denominator). The fitting error may be calculated for various parameter pairs and, finally, the value used for VTA prediction is obtained as the sum of the FERs of the parameter pairs. The parameter pairs may include selected or all parameters of the repolarization parameter set.

In step 22, the Mahalanobis distance (MD) and the total FER, i.e. the FER sum, are compared with respective predetermined threshold values. If either or both of the measures has reached or crossed the respective threshold value, a significant repolarization change is detected. In this case, the patient monitor examines in step 27 whether the control parameters are able to explain the detected change. If this is the case, it is decided that the significant change detected is due to a non-critical reason and normal state is indicated (step 29). However, if none of the control parameters is able to explain why a fast and significant change was detected in the repolarization, an alarm of increased risk of VTA is raised in step 28.

In detection branch 13, slow changes in the repolarization are monitored by determining a weighted average WA of selected or all repolarization parameters (step 23). Thus, the following equation applies for the weighted average WA: WA=C1×P1+C2×P2+ . . . +Cn×Pn, where P1 to Pn are n parameters selected from the repolarization parameters and C1 to Cn are predefined coefficients that may be optimized in advance using training data obtained from a large patient group. The purpose of the optimization is to find the coefficient values that give maximal change of WA for patients with VTA episode while giving maximally flat WA for arrhythmia free control cases. The slope of the WA signal may be maximized, for example, by using standard optimization methods. In one embodiment, WA may be calculated based on all five repolarization parameters mentioned above.

If it is detected in step 24 of branch 13 that the weighted average remains below its threshold value, normal state is indicated (step 29), provided that no significant change is detected in branch 14. Similarly, if it is detected in branch 14 that none of the Mahalanobis distance and the fitting error ratio has reached or exceeded the respective threshold value (step 22/no), normal state is indicated (step 29), provided that no significant change is detected in branch 13.

However, if it is detected in step 24 of branch 13 that the WA has reached or crossed the predetermined threshold, the process jumps directly to step 28 to produce an alarm of increased risk of VTA. Thus, if a significant change is detected in the detection of slow changes, the change is always regarded as an increased risk of a ventricular tachyarrhythmia event and an alarm is raised.

Figure 3:
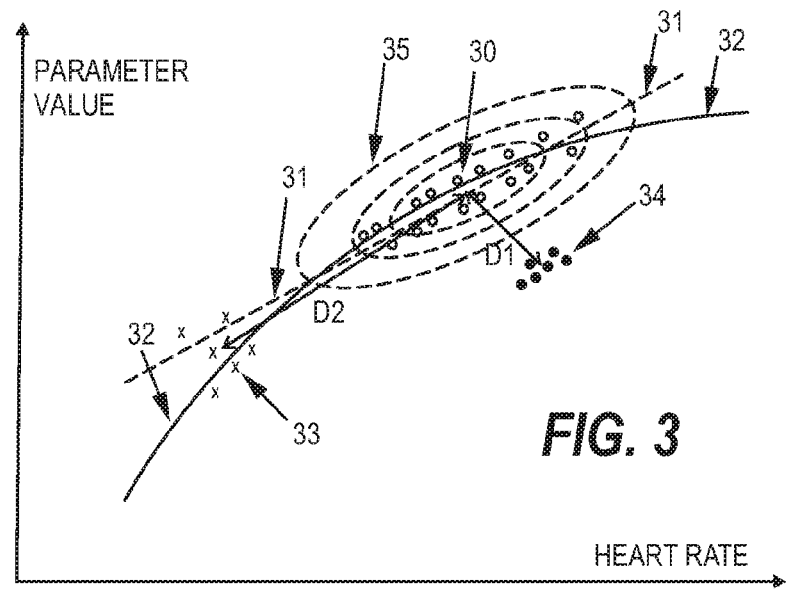
FIG. 3 illustrates the effectiveness of two successive measures for detecting fast repolarization changes that may predict a ventricular tachyarrhythmia event.

In a further embodiment of the method/apparatus, only one of the detection branches may be utilized. Furthermore, although two branches are used, only one of the Mahalanobis distance and FER may be used as an indicator of a significant change in branch 14. However, the use of two measures in branch 14 improves the performance of VTA prediction. This is illustrated in FIG. 3, where the parameter samples shown as small circles 30 represent the samples used to determine the above-mentioned covariance and dependency between the parameter and heart rate. The estimated dependency is shown as dashed line 31, while the continuous curve 32 shows the true dependency between the parameter and heart rate. The crosses 33 and the black dots 34 represent, respectively, two possible changes occurring after samples 30. The figure further illustrates that Euclidean distance is not a good measure of change: Euclidean distance D2 is significantly greater than Euclidean distance D1 despite the fact that samples 33 represent rather normal values for the parameter at slower heart rates. The equidistance lines of the Mahalanobis distance are illustrated as ellipsoids 35 around the mean value of the samples. Thus, Mahalanobis distance gives approximately the same distance for the two possible sample sets. However, in terms of the fitting error ratio, samples 34 are notably further away from the estimated linear dependency line 31 than samples 33. Consequently, a significant change is detected in the embodiment of FIG. 2 when progressing from samples 30 to samples 34 but not when progressing from samples 30 to samples 33.

The repolarization parameters that may be employed are parameters that have demonstrated to possess predictive potential in terms of VTA or parameters that are related to the mechanisms of arrhythmias. As mentioned above, in one embodiment of the method five repolarization parameters may be employed, which are T wave amplitude, T wave asymmetry, T wave area, ST level, and ST slope. ST level may be defined as the mean signal amplitude in the ST segment, while ST slope may be defined as the slope of a linear fit to the samples of the ST segment. Also variation parameters may be used, such as parameters indicative of variation in T wave. These parameters may include T peak amplitude variation (variance of T wave amplitude measured at its peak), T peak temporal variation (variance of temporal position of T wave peak) and ST lability (maximal variation in ST segment), for example.

The purpose of the control parameters is to detect changes that affect repolarization but are not related to real changes in the cardiac state or myocardial repolarization. At least part of the control parameters may be indicative of the stability of depolarization. Such parameters include QRS amplitude, QRS-T angle, and position of QRS maxima, for example. In addition, an abrupt change in the position of T wave maxima may cause unwanted discontinuity in the measurement of morphology parameters. Thus, the position of T wave maxima may be used as a control parameter. Furthermore, parameters indicative of the quality of the measured ECG signal may be used as control parameters. In addition, detection of other types of arrhythmia events, such as atrial fibrillation, may be used as a control parameter. Although the control parameters are above used to filter out false positive detections of fast changes only, one or more control parameters may be used to filter out false positive detections of slow changes too. This concerns especially the control parameters indicative of signal quality.

An example of a change that affects repolarization but does not necessarily indicate an imminent VTA episode is a sudden bundle branch block, where conduction abnormalities in depolarization cause significant and unpredicted changes in the QRS wave. This will also cause significant changes in the T-wave, which will in turn be detected as a fast repolarization change in branch 14. However, the detection of the fast repolarization change will not cause a false alarm, since it is detected in step 25 that a control parameter changes abruptly substantially simultaneously as the fast repolarization change is detected. Consequently, in step 25 the decision rule may be, for example, that the control parameters explain the detected repolarization change (step 25/yes) if one or more of the above control parameters change abruptly substantially at the same time as the fast repolarization change is detected. For some of the control parameters, such as signal quality parameters, a change in a given direction may be required, i.e. any simultaneous change may not be sufficient to invalidate a detected repolarization change.

Figure 4:
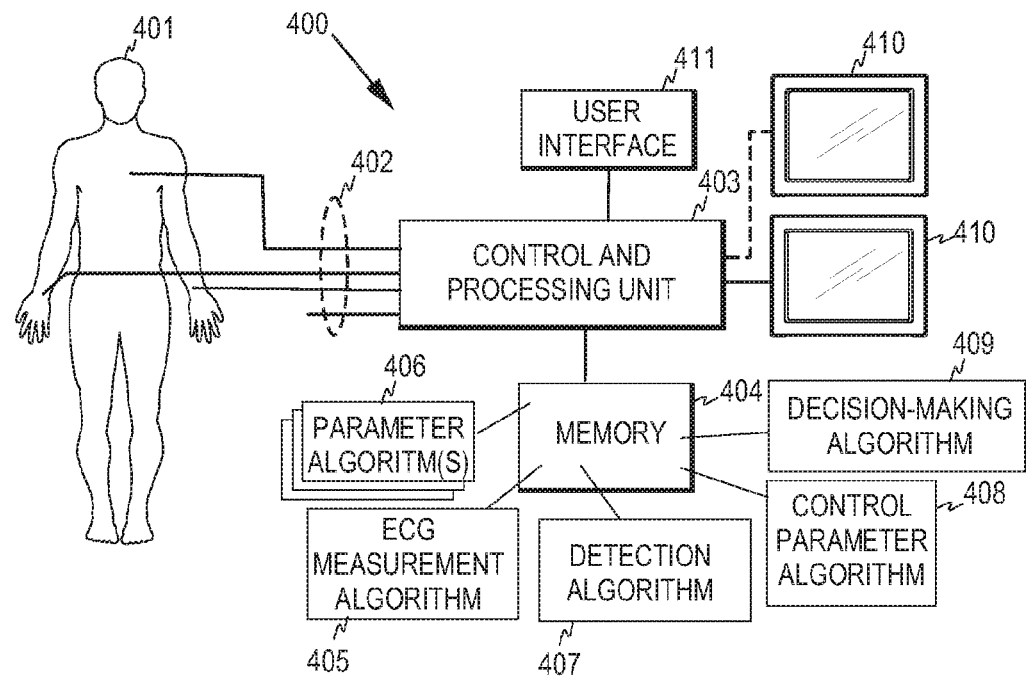
FIG. 4 illustrates an embodiment of an ECG monitoring apparatus/system.

FIG. 4 illustrates one embodiment of a monitoring apparatus/system 400 provided with a capability to predict an imminent ventricular tachyarrhythmia event of a subject 401. A monitoring apparatus/system normally acquires a plurality of physiological signals 402 from the subject, where one physiological signal corresponds to one measurement channel. The physiological signals typically comprise several types of signals, such as ECG, EEG, blood pressure, respiration, and plethysmographic signals. Based on the raw real-time physiological signal data obtained from the subject, a plurality of physiological parameters may be determined. A physiological parameter here refers to a variable calculated from the waveform data of one or more of the physiological signals acquired from the subject. If a physiological parameter is derived from more than one physiological signal, i.e. from more than one measurement channel, the said physiological signals are usually of the same signal type. The physiological parameter may thus also represent a waveform signal value determined over a predefined period of time, although the physiological parameter is typically a distinct parameter derived from one or more measurement channels, such as heart rate derived from an ECG signal or an $SpO_2$ value derived from a plethysmographic signal. Each signal parameter may be assigned one or more alarm limits to alert the nursing staff when the parameter reaches or crosses the alarm limit.

The physiological signals 402 acquired from the subject 401 are supplied to a control and processing unit 403 through a pre-processing stage (not shown) comprising typically an input amplifier and a filter, for example. The control and processing unit converts the signals into digitized format for each measurement channel. The digitized signal data may then be stored in the memory 404 of the control and processing unit.

As the disclosed measurement concerns ECG measurement, the apparatus/system is discussed in terms of the ECG measurement in this context. However, it is to be noted that no real ECG electrode placement is shown in FIG. 4. For the ECG measurement, the control and processing unit may be provided with a separate ECG measurement algorithm 405 adapted to acquire the ECG lead signal data from the subject. For the determination of the ECG related parameters, the control and processing unit may further be provided with one or more ECG parameter algorithms 406 adapted to calculate ECG related parameters, including the repolarization parameters and heart rate. The control and processing unit may further be provided with a detection algorithm 407 adapted to detect slow and/or fast changes in the repolarization parameters, with a control parameter algorithm 408 adapted to determine the control parameters, and with a decision-making algorithm 409 for making the decision on the VTA risk level. A display control algorithm (not shown) is adapted to display the alarms to the user on the screen of a display unit 410.

Figure 5:
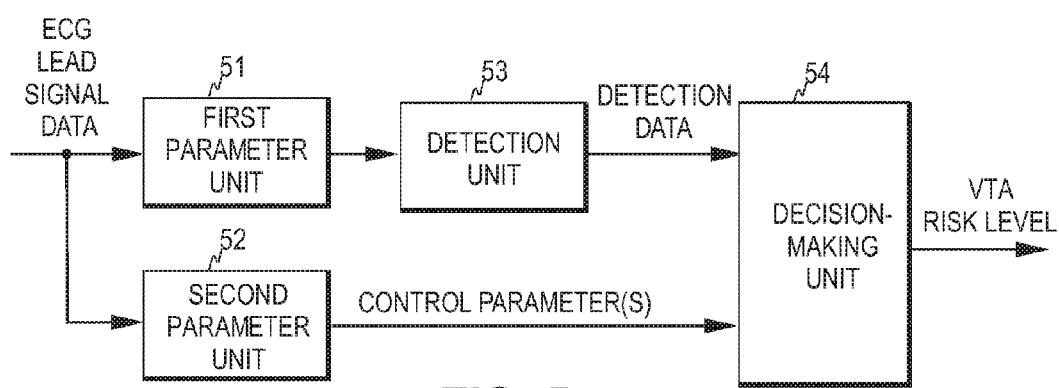
FIGS. 5 and 6 illustrate the operational entities of the ECG monitoring apparatus/system in terms of the prediction of an imminent ventricular tachyarrhythmia.

Consequently, in terms of the disclosed VTA prediction process, the functionalities of the control and processing unit 403 may be divided into the units shown in FIG. 5. A first parameter unit 51 is configured to determine the repolarization parameters based on the ECG lead signal data and a second parameter unit 52 is configured to determine the control parameters. A detection unit 53 is adapted produce the change indication variables (WA/MD/FER) and to detect slow and/or fast changes, and a decision-making unit 54 is configured to make a decision on the VTA risk level based on the detections and the control parameters. The detection unit may be provided with one or two detection branches (13 and/or 14) and the detection of fast changes may be configured to determine one or two change measures (MD and/or FER).

Figure 6:
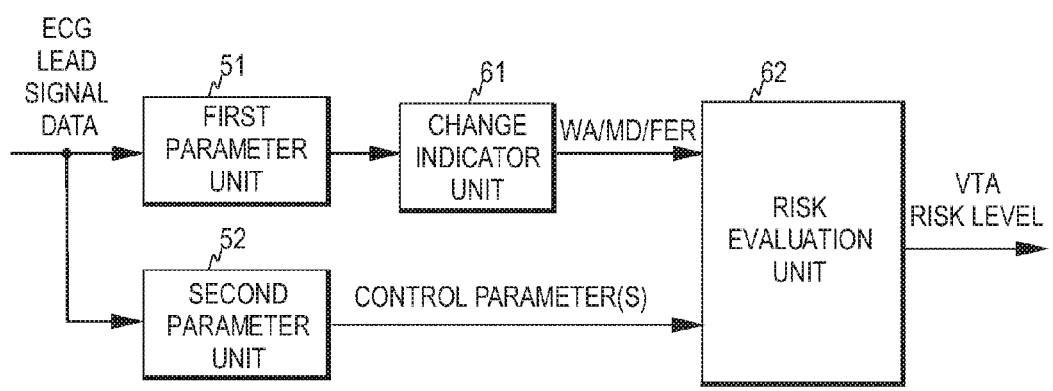

It is to be noted that FIGS. 4 and 5 illustrate an example of the division of the functionalities of the control and processing unit in logical sense and in view of the VTA risk prediction. The functionalities may also be divided according FIG. 6 so that the change indication variables (i.e. WA/MD/FER) and the control parameters are processed in an entity, termed risk evaluation unit 62, which is adapted to define the risk level of a potential ventricular tachyarrhythmia event based on this input data. The unit 61 adapted to produce the change indication variables is termed a change indicator unit in the figure. Furthermore, in a real apparatus the functionalities may be distributed in different ways between the elements or units of the apparatus/system. Some of the data, such the coefficients needed for the determination of the weighted average, may even be received from a network element.

A conventional patient monitor may also be upgraded to enable prediction of VTA risk level. Such an upgrade may be implemented, for example, by delivering to the monitor a plug-in unit that may be provided with the necessary software portions for enabling the control and processing unit to determine the repolarization parameters needed, detect the changes in the repolarization parameters, and to make the decision on the risk level. The contents of the software portions may vary depending on the existing features or capabilities of the monitor, for example on whether any of the parameters needed for the prediction is available in the monitor. The plug-in unit may be delivered, for example, on a data carrier, such as a CD or a memory card, or the through a telecommunications network.

The above solution provides a tool that is able to predict VTA events efficiently within a few hours before the onset of the actual event. This gives the nursing staff plenty of time to change the care procedures to avoid the imminent VTA episode and to prepare the rescue procedures against the possible onset of the episode. This results in significantly better chances of survival and reduced deterioration of the cognitive state, which also translates to earlier hospital discharge and decreased need for expensive rehabilitation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for predicting ventricular tachyarrhythmia, the method comprising:
   determining a set of repolarization parameters indicative of ventricular repolarization in a subject's heart, wherein the determining is performed in successive time segments, thereby to obtain a time series of the set of repolarization parameters;
   producing, based on the time series, at least one trend variable indicative of slow changes in the ventricular repolarization of the heart and at least one fast change variable indicative of fast changes in the ventricular repolarization of the heart;
   determining at least one control parameter indicative of occurrences of events that affect the ventricular repolarization of the heart without increasing risk of ventricular tachyarrhythmia; and
   predicting risk of potential ventricular tachyanhythmia based on the at least one trend variable and the at least one fast change variable,
   wherein the predicting comprises discarding at least the fast change variable based upon the at least one control parameter.

2. The method according to claim 1, wherein the producing comprises
   producing the trend variable, in which the trend variable represents a weighted average of a plurality of repolarization parameters, wherein the plurality of repolarization parameters belong to the set of repolarization parameters;
   estimating a relationship between a repolarization parameter and heart rate, wherein the repolarization parameter belongs to the set of repolarization parameters and wherein the estimating is performed for at least one repolarization parameter, thereby to obtain at least one relationship; and
   producing the at least one fast change variable, in which the at least one fast change variable comprises a first variable indicative of similarity between successive sets of repolarization parameters in the time series and a second variable indicative of change in difference between a first and a second group of repolarization parameters, wherein the first group is obtained through the at least one relationship and the second group belongs to the time series.

3. The method according to claim 2, wherein the producing comprises producing the first variable and a second variable, in which the first variable represents Mahalanobis distance between selected repolarization parameters obtained in successive sets of the time series and the second variable represents ratio of two differences obtained through the at least one relationship in successive time segments, wherein each difference represents difference between repolarization parameters estimated through the at least one relationship and respective repolarization parameters obtained in the time series.

4. The method according to claim 2, wherein the predicting comprises
   comparing the trend variable with a predetermined threshold; and
   detecting increased risk of ventricular tachyarrhythmia when the trend variable reaches the predetermined threshold.

5. The method according to claim 4 wherein the increased risk of ventricular tachyarrhythmia is detected when the trend variable reaches the predetermined threshold regardless of the at least one control parameter.

6. The method according to claim 1, wherein the determining comprises determining the set of repolarization parameters, in which the set comprises morphology parameters indicative of T wave morphology.

7. The method according to claim 6, wherein the determining comprises determining the set of repolarization parameters, in which the set comprises T wave amplitude, T wave asymmetry, T wave area, ST level, and ST slope.

8. The method according to claim 1, wherein the set of repolarization parameters comprises morphology parameters indicative of T wave morphology.

9. The method according to claim 8, wherein the set of repolarization parameters comprises T wave amplitude, T wave asymmetry, T wave area, ST level, and ST slope.

* * * * *